US010870808B2

(12) United States Patent
Baldridge et al.

(10) Patent No.: US 10,870,808 B2
(45) Date of Patent: Dec. 22, 2020

(54) ISOMERIZATION AND CATALYTIC ACTIVATION OF PENTANE-ENRICHED HYDROCARBON MIXTURES

(71) Applicant: PHILLIPS 66 COMPANY, Houston, TX (US)

(72) Inventors: Anthony O. Baldridge, Bartlesville, OK (US); Neal D. McDaniel, Ochelata, OK (US); James A. Suttil, Bartlesville, OK (US); Jianhua Yao, Bartlesville, OK (US); Edward C. Weintrob, Owasso, OK (US); Matthew J. Wulfers, Collinsville, OK (US); Bruce B. Randolph, Bartlesville, OK (US); Maziar Sardashti, Timnath, CO (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 16/855,312

(22) Filed: Apr. 22, 2020

(65) Prior Publication Data

US 2020/0339896 A1 Oct. 29, 2020

Related U.S. Application Data

(60) Provisional application No. 62/838,057, filed on Apr. 24, 2019.

(51) Int. Cl.
*C10G 69/12* (2006.01)
*C10G 45/64* (2006.01)
(Continued)

(52) U.S. Cl.
CPC .......... *C10G 69/123* (2013.01); *C07C 5/2775* (2013.01); *C10G 45/64* (2013.01);
(Continued)

(58) Field of Classification Search
CPC .......... C07C 11/02; C07C 11/10; C07C 4/06; C07C 5/03; C07C 6/04; C07C 2/58;
(Continued)

(56) References Cited

U.S. PATENT DOCUMENTS

| 7,485,768 B1* | 2/2009 | Rice ...................... C10G 35/00 208/133 |
| 2010/0036182 A1* | 2/2010 | Forestiere ............... C07C 11/06 585/251 |

(Continued)

OTHER PUBLICATIONS

Schallmoser, S.; Ikuno, T.; Wagenhofer, M.F.; Kolvenbach, R.; Haller, G.L.; Sanchez-Sanchez, M.; Lercher, J.A., "Impact of the Local Environment of Bronsted Acid Sites in ZSM-5 on the Catalytic Activity in N-Pentane Cracking", J. Catal. 2014, vol. 316, pp. 93-102.

(Continued)

*Primary Examiner* — Ali Z Fadhel
(74) *Attorney, Agent, or Firm* — Phillips 66 Company (57) ABSTRACT

Processes for producing liquid transportation fuels by converting a hydrocarbon feed stream comprising both isopentane and n-pentane. The hydrocarbon feed stream is separated into a first fraction that predominantly comprises isopentane and a second fraction that predominantly comprises n-pentane and some C6 paraffins. The first fraction is catalytically activated to an activation effluent comprising olefins and aromatics, while the second fraction is isomerized to convert at least a portion of the n-pentane to isopentane, then combined with the hydrocarbon feed stream to allow the newly-produced isopentane to be separated into the first fraction. The process yields products that are suitable for use as a blend component of liquid transportation fuels.

20 Claims, 6 Drawing Sheets

(51) Int. Cl.
*C10G 65/04* (2006.01)
*C07C 5/27* (2006.01)
*C07C 9/16* (2006.01)
*C07C 5/22* (2006.01)

(52) U.S. Cl.
CPC ......... *C10G 65/043* (2013.01); *C10G 69/126* (2013.01); *C07C 5/22* (2013.01); *C07C 9/16* (2013.01); *C10G 2300/1081* (2013.01)

(58) Field of Classification Search
CPC .......... C07C 2/12; C07C 2/865; C07C 5/373; C07C 5/41; C07C 2/864; C07C 9/15; C07C 9/18; C07C 5/333; C07C 9/16; C07C 9/14; C07C 2/74; C07C 2/54; C07C 2/56; C07C 2/42; C07C 4/10; C07C 4/02; C07C 5/32; C07C 6/10; C07C 6/123; C07C 6/126; C07C 5/321; C07C 2/76; C07C 2529/40; C10L 1/04; C10G 59/06; C10G 2400/30; C10G 2300/1081; C10G 2400/20; C10G 9/00; C10G 57/005; C10G 29/205
See application file for complete search history.

(56) References Cited

U.S. PATENT DOCUMENTS

2010/0041930 A1\* 2/2010 Gartside ................ C07C 11/06
585/314
2016/0168054 A1\* 6/2016 Kalnes ..................... C07C 6/10
585/312

OTHER PUBLICATIONS

Jentoft, F.C.; Gates, B.C., "Solid-Acid-Catalyzed Alkane Cracking Mechanisms: Evidence From Reactions of Small Probe Molecules", Top. Catal, 1997, vol. 4, pp. 1-13.

Sie, S.T., "Acid-Catalyzed Cracking of Paraffinic Hydrocarbons 1. Discussion of Existing Mechanisms and Proposal of a New Mechanism", Ind. Eng. Chem. Res. 1992, vol. 31, pp. 1991-1889.

Miyaji, A.; Iwase, Y. Nishioba; T.; Long; N.Q.; Motokura; K.; Baba, T.; "Influence of Zeolite Pore Structure on Product Selectivities for Protolysis and Hydride Transfer Reactions in the Cracking of N-Pentane", Phys, Chem. Chem. Phys. 2015, vol. 17, pp. 5014-5032.

Narbeshuber, T.F.; Vinek, H.; Lercher, J.A., "Monomolecular Conversion of Light Alkanes Over H-ZSM-5", J. Catal, 1995, vol. 157, pp. 388-395.

\* cited by examiner

ISOMERIZATION AND CATALYTIC ACTIVATION OF PENTANE-ENRICHED HYDROCARBON MIXTURES

CROSS-REFERENCE TO RELATED APPLICATIONS

This application is a non-provisional application which claims the benefit of and priority to U.S. Provisional Application Ser. No. 62/838,057 filed Apr. 24, 2019, titled "Isomerization and Catalytic Activation of Pentane-Enriched Hydrocarbon Mixtures," which is hereby incorporated by reference in its entirety.

STATEMENT REGARDING FEDERALLY SPONSORED RESEARCH OR DEVELOPMENT

None.

FIELD OF THE INVENTION

The present disclosure generally relates to processes and systems that converts at least a portion of the n-pentane in a light hydrocarbon feed stream to isopentane, followed by an activation step and subsequent upgrading to larger hydrocarbons in either an alkylation reactor or oligomerization reactor. The processes and systems produce hydrocarbons suitable for use as a blend component of a liquid transportation fuel.

BACKGROUND

A large surplus of pentanes are available in the petroleum refining industry, arising predominantly from the increased production of light hydrocarbons from U.S. shale formations and also from limits on the quantity of volatile components that can be blended into finished transportation fuels, which must adhere to regulations on maximum vapor pressure. Unfortunately, conventional processes for upgrading light alkanes to value-added products are not well-suited for hydrocarbon feed streams that primarily comprise pentanes (i.e., isopentane and n-pentane). Therefore, it would be beneficial to find improved processes and systems for efficiently converting pentanes to more valuable products, including transportation fuels and chemicals, while minimizing the production of C1-C4 light paraffins.

The inventive processes disclosed herein provide an improved upgrading route for pentane-rich fuel blend-stocks and other pentane-rich streams that do not meet government specifications for a transportation fuel. The inventive processes and systems provide enhanced yields of upgraded products that may be suitable for use as transportation fuels or other value-added chemical products.

BRIEF SUMMARY OF THE DISCLOSURE

Certain embodiments comprise an method for converting a hydrocarbon feed stream comprising pentanes to produce a liquid transportation fuel, the method comprising: a) providing a hydrocarbon feed stream comprising at least 50 wt. % pentanes, including both n-pentane and isopentane; b) at least partially separating the hydrocarbon feed stream in a separator to produce: a first fraction that comprises at least 80% of the isopentane present in the hydrocarbon feed stream (on a molar basis), and that further comprises at least 90% of hydrocarbons present in the hydrocarbon feed stream (on a molar basis) that are characterized by a vapor pressure equal to or greater than the vapor pressure of isopentane, and a second fraction that comprises at least 80% of the n-pentane content of the hydrocarbon feed stream (on a molar basis) and at least 90% of hydrocarbons from the hydrocarbon feed stream that contain six or more carbons (on a molar basis); c) contacting the first fraction with an activation catalyst at a temperature and a pressure that facilitates catalytic activation of at least a portion of the first fraction by the activation catalyst to produce an activation effluent comprising olefins containing from two to five carbon atoms, monocyclic aromatics and unconverted alkanes containing from two to five carbon atoms; d) removing a first portion of the second fraction for use as blend component of a liquid transportation fuel; e) contacting a second portion the second fraction with at least one isomerization catalyst in an isomerization reactor that is maintained at a temperature and a pressure that facilitates the isomerization of at least a portion of n-pentane in the second fraction to produce isopentane, thereby producing an isomerization effluent characterized by an increased ratio of isopentane to n-pentane (on a wt. % basis) relative to the isopentane to n-pentane ratio of the hydrocarbon feed stream; f) combining the isomerization effluent with the hydrocarbon feed stream of a).

Some embodiments further comprise separating the liquid hydrocarbons fraction into an aromatics fraction and an unreacted C5/C6 hydrocarbons fraction, where the aromatics fraction comprises monocyclic aromatics suitable for use as a blend component of gasoline and the unreacted C5/C6 hydrocarbons fraction comprises alkanes and olefins containing from five to six carbons that are either mixed with the hydrocarbon feed stream or are recycled to the separation zone of a.).

In some embodiments, the hydrocarbon feed stream comprises at least 30 wt. % pentanes; optionally, at least 50 wt. % pentanes; optionally, at least 70 wt. % pentanes. In some embodiments, the hydrocarbon feed stream is contacted with one or more isomerization catalysts contained within in multiple reaction zones that are arranged in a series configuration.

In some embodiments, the activation catalyst comprises one or more zeolites characterized by a Si/Al ratio ranging from 12 to 80. In some embodiments, the activation catalyst comprises ZSM-5 zeolite. In some embodiments, the activation catalyst facilitates carbon-hydrogen bond activation that leads to at least one of olefinization, dimerization, oligomerization, dehydrogenation and aromatization.

In some embodiments, the temperature in the activation reactor is maintained at a temperature in the range from 500° C. to 625° C.; optionally, in the range from 525° C. to 600° C.; optionally, in the range from 550° C. to 600° C.; optionally, in the range from 525° C. to 600° C.

In some embodiments, the temperature in the activation reactor is maintained at a temperature and a pressure in the range from 15 psig to 100 psig; optionally, in the range from 15 psig to 75 psig; optionally, in the range from 12 psig to 60 psig; optionally, in the range from 20 psig to 60 psig.

Some embodiments further comprise adding a diluent to the first fraction prior to the contacting with the activation catalyst, wherein the diluent is characterized as less likely to react with the activation catalyst than the first fraction is likely to react with the activation catalyst at the conditions of temperature and pressure that are maintained in the activation reactor.

Some embodiments further comprise adding a diluent to the first fraction prior to the contacting with the activation catalyst, wherein the diluent does not react with activation catalyst at the conditions of temperature and pressure that are maintained in the activation reactor. In some embodiments, the diluent is added in an amount that alters the specificity of the activation catalyst to increase the production of olefins, decrease the production of aromatics, or combinations thereof, thereby increasing the ratio of olefins to aromatics in the resulting activation effluent.

In some embodiments, the diluent is added in an amount that is effective to produce an activation effluent characterized by an olefins to aromatics ratio in the range of 0.5 to 2.0. In some embodiments, the diluent is added in an amount that is effective to produce an activation effluent characterized by an olefins to aromatics ratio in the range of 0.5 to 1.0. In some embodiments, the diluent is selected from methane, ethane, propane, n-butane, i-butane and combinations thereof.

In certain embodiments, the gaseous light hydrocarbons fraction is separated into a light paraffins fraction comprising C1-C4 paraffins and a light olefins fraction comprising C1-C4 olefins and hydrogen, and at least a portion of the light paraffins fraction is combined with the first fraction upstream from the activation reactor to serve as the diluent.

In certain embodiments, at least a portion of the second fraction is passed through multiple isomerization reactors that are arranged in series configuration, wherein each of the multiple reactors contains at least one isomerization catalyst and is maintained at a temperature and a pressure that facilitates the isomerization of n-pentane to isopentane by the at least one isomerization catalyst.

BRIEF DESCRIPTION OF THE DRAWINGS

A more complete understanding of the present invention and benefits thereof may be acquired by referring to the follow description taken in conjunction with the accompanying drawings in which.

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

The present disclosure provides processes and systems for converting a mixture of light hydrocarbons to liquid transportation fuels. More specifically, it pertains to the conversion of any hydrocarbon mixture that predominantly comprises pentanes to generate upgraded products that may be sold as a value-added chemical or utilized as a blend component of a liquid transportation fuel.

Generally speaking, the inventive processes and systems described herein utilize a hydrocarbon feed stream that comprises both isopentane (i-C5) and n-pentane (n-C5). The process performs an initial separation of the hydrocarbon feed stream to produce a first fraction that predominantly comprises i-C5 and a second fraction that predominantly comprises n-C5 and C6+ hydrocarbons. The first fraction is then catalytically-activated in an activation reactor to convert at least a portion of the i-C5 to olefins and aromatics. A portion of the second fraction is either diverted to blended into liquid transportation fuels or isomerized in an isomerization reactor to convert at least a portion of the n-C5 in the second fraction to i-C5, and a portion of any n-hexane (n-C6) in the second fraction to iso-hexane isomers. The resulting isomerization effluent is then recycled to the initial separation step to allow separation of the additional i-C5 produced in the isomerization reactor, which is then directed to the activation reactor along with the first fraction.

The inventive processes and systems allow an increased percentage of the hydrocarbon feed stock to be catalytically activated to produce predominantly olefins and aromatics, while minimizing the percentage of the feed stock that is converted to less desirable C1-C4 paraffins. The resulting isomerization effluent is then catalytically activated under conditions of temperature and pressure (typically measured at the inlet of the activation reactor) that maximize the catalytic conversion of the isomerization effluent to olefins and aromatics, while minimizing the undesirable production of C1-C4 light hydrocarbons, often referred to as fuel gas.

Certain embodiments of the inventive processes and systems further upgrade the resulting activation effluent by contacting the activation effluent with an oligomerization and/or alkylation catalyst at a temperature and pressure that facilitates conversion of the activation effluent to value-added chemicals and/or products suitable for use as a liquid transportation fuel blend component. This additional upgrading may be preceded by compressing (and optionally, partially condensing) the activation effluent in order to facilitate the subsequent oligomerization and/or alkylation step.

As mentioned, the hydrocarbon feed stream predominantly comprises a mixture of pentane isomers (C5). The hydrocarbon feed stream may additionally comprise C2-C4 hydrocarbons, C6-C7 hydrocarbons, or both. The hydrocarbon feed stream generally comprises both i-C5 and n-C5 pentane isomers. In certain embodiments, the hydrocarbon feed stream comprises at least 10 wt. % of a mixture of pentane isomers; optionally, at least 20 wt. %, optionally, at least 30 wt. %, optionally, at least 40 wt. %, optionally at least 50 wt. %, optionally, at least 60 wt. %, or optionally, at least 70 wt. %. of a mixture of pentane isomers. In certain embodiments, the hydrocarbon feed stream may be obtained by processing a stream of natural gas liquids to remove lighter components (i.e., C1-C4) by way of conventional natural gas processing technologies that are well-characterized, such as de-methanizer, de-ethanizer, de-propanizer and de-butanizer fractionation columns, although such separation is not essential. A typical result of such processes is commonly characterized as natural gasoline, comprising about 72 wt. % pentanes, with the remainder predominantly comprises hexane. In certain embodiments, the hydrocarbon feed stream comprises less than 30 wt. %, optionally, less than 20 wt. %, optionally, less than 10 wt. % of hydrocarbons containing four or fewer carbon atoms.

Figure 1:
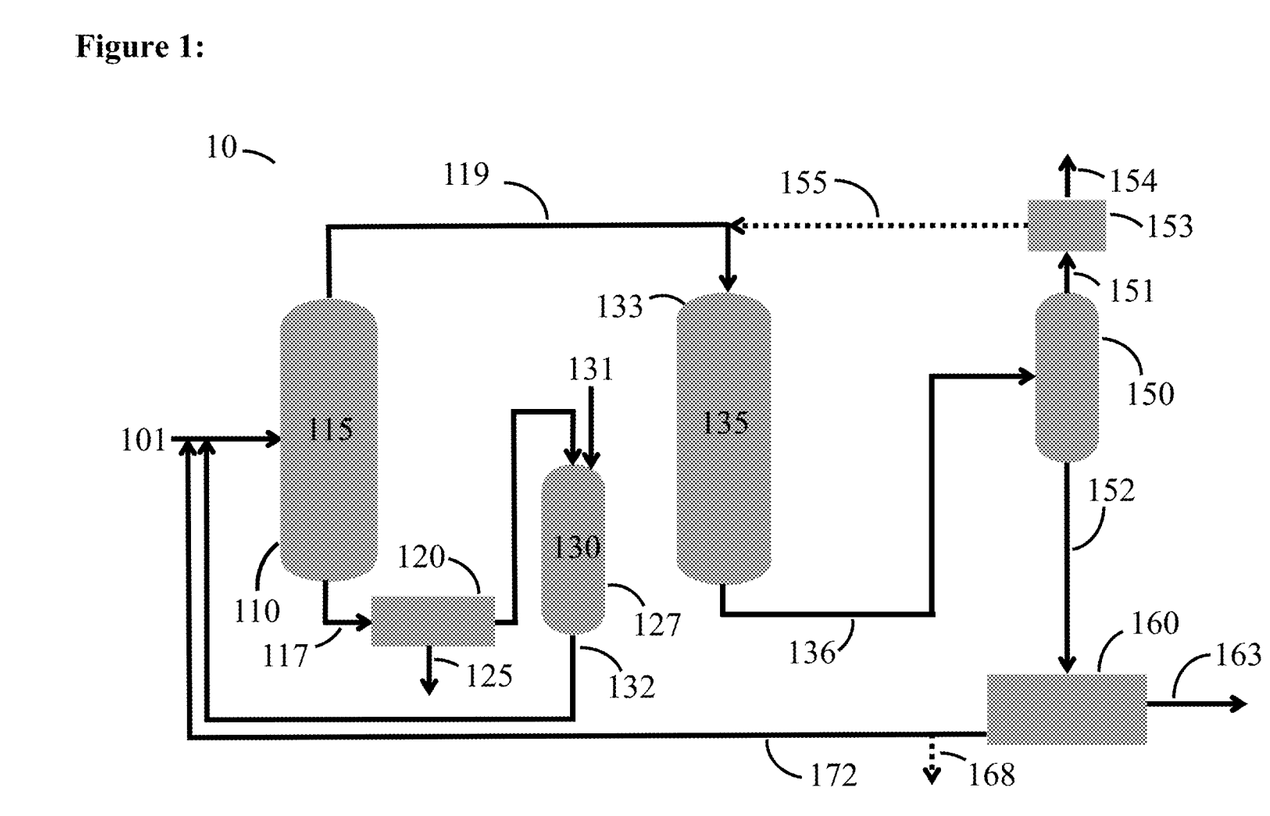
FIG. 1 is a diagram depicting a first embodiment of the inventive processes and systems.

A first embodiment of the inventive processes and systems is illustrated by the process flow-diagram of FIG. 1. A hydrocarbon feed stream 101 comprising both n-pentane (nC5) and isopentane (iC5) is converted in a system 10. The hydrocarbon feed stream 101 is received by a first separator 110 that operates to separate the feed stream 101 into a first fraction 119 that comprises an increased wt. % of isopentane (i-C5) relative to the feed stream 101, and a second fraction 117 that comprises an increased wt. % of n-pentane relative to the feed stream 101. The second fraction further comprises a large majority of any C6 and larger (C6+) hydrocarbons originally present in the hydrocarbon feed stream 101. The first separator 110 may operate using conventional separation technology 115 to separate the i-C5 isomer from the remaining compounds present within the C5-rich hydrocarbon feed stream. Alternatively, any other separation technology may be used to assist in separating i-C5 from n-C5 to produce the first fraction and the second fraction.

Following separation, the first fraction 119 is conveyed to an activation reactor 133 containing an activation catalyst 135. The activation reactor 133 is operable to maintain a temperature and pressure that is suitable to facilitate conversion of the first fraction 119 to a first effluent 136.

Speaking generally, the temperature within the activation reactor (typically measured at, or proximal to, the inlet of the activation reactor) is maintained in the range from 500° C. to 650° C.; optionally, within the range from 525° C. to 625° C.; optionally, within the range from 525° C. to 600° C.; optionally, within the range from 550° C. to 600° C.; optionally, within the range from 550° C. to 575° C.; optionally, within the range from 575° C. to 600° C.

The pressure maintained within the activation reactor generally ranges from 15 psia (103 kpa) to 165 psia (1138 kpa); Optionally, in the range from 15 psig to 100 psig.; Optionally, in the range from 15 psig to 75 psig.; Optionally, in the range from 20 psig to 60 psig.; Optionally, in the range from 20 psig to 50 psig.

Speaking generally, the activation catalyst may comprise a single catalyst, or a mixture of different catalysts that contact the alkanes present in a given feed stream and facilitates at least one of dehydrogenation, cracking, and aromatization of the alkanes, thereby producing upgraded products including olefins and aromatics. Favored catalysts include supported or unsupported solid acids, metals, metal chalcogenides, or metal pnictogenides, including (but not limited to) structured and amorphous silica-aluminas, structured and amorphous solid phosphoric acids, clays, other metal oxides, metal sulfates, or metal phosphates, and graphite-supported materials. In certain embodiments, ZSM-5 zeolite catalysts are utilized that are characterized by Si/Al ratios ranging from 12-80, optionally ranging from 35 to 50. Optionally, one or more elements may optionally be impregnated on the zeolite catalyst, including one or more of Ga, Pt, Ni, Mn, Mg, Fe, Cr, P, Cu, La, Sr and F, but are not required for operability of the invention.

Generally speaking, dehydrogenation catalysts are not utilized for paraffin activation in the instant inventive process. A sufficient concentration of intermediate olefins can be generated through a combination of thermal dehydrogenation and catalytic cracking such that typical dehydrogenation metals can be avoided without significantly decreasing product yield. Known dehydrogenation catalysts are prone to fouling by sulfur and nitrogen contaminants that are often present in hydrocarbon feed streams derived from petroleum, so the ability to operate in the absence of sensitive catalytic materials is highly advantageous.

The inventive process generally takes advantage of the large reactivity difference to catalytic activation of n-C5 relative to i-C5. For example, when contacted with a solid acid catalyst at a temperature in excess of 550 C, the measured activation rate of i-C5 is up to four-fold that of n-C5, even when both isomers are simultaneously present in the same reactor. Thus, an at least partial separation of the mixed pentanes feed stream to form a first fraction that largely comprises i-C5 and a second fraction that retains a large majority of the n-C5 in the feed stream, which allows the iC5 to be selectively activated at conditions comprising a lower temperature (e.g., 550° C. versus 600° C.) and a pressure that decreases selectivity to C1-C4 light paraffins during catalytic activation, while maximizing the selectivity of the activation toward the production of value-added products (such as olefins and aromatics).

Table 1 (below) illustrates the difference in the activation reactivity of i-C5 versus n-C5 over a microporous silica-alumina catalyst. Feed streams comprising either 100 wt. % i-C5 or 100 wt. % n-C5 were each catalytically activated in separate experiments utilizing temperatures of either 600° C. or 550° C. The conversion and product distribution for i-C5 are shown in Table 1, columns 2 and 3, while similar results for the activation of n-C5 are shown in Table 1, columns 4 and 5. The data shows that when comparing the activation of pentane isomers, conversion of i-C5 to olefins and aromatics is possible at a temperature about 50° C. less than is required for equivalent conversion of n-C5. To be clear, we observed that activation of the i-C5 feed stream at 550° C. converted about the same weight percentage of the feed stream as did activation of n-C5 at 600° C. using the same WHSV. Further, utilizing a decreased temperature of 550° C. for activation of the i-C5 feed stream advantageously decreased the production of C1-C4 light paraffins from 21.0% to 19.4% by increasing the product distribution toward olefins rather than aromatic products. Thus, the ability to separate the i-C5 isomer from n-C5 isomer (and any C6+ hydrocarbons), and separately activate the i-C5 enriched mixture at relatively reduced temperature results in approximately equivalent total conversion of the hydrocarbon feed stream, while decreasing the formation of undesired C1-C4 light paraffins.

Referring again to the embodiment depicted in FIG. 1, the second fraction 117 is directed to a storage vessel 120 that is operable to both receive the second fraction, and to optionally divert at least a portion of the second fraction to produce a blending fraction 125 that may be blended directly into a liquid hydrocarbon transportation fuel (e.g., gasoline). The remainder of the second fraction is conveyed from the storage vessel 120 to a isomerization reactor 127 that contains an isomerization catalyst 130 and is operable to receive a flow of hydrogen gas 131, and further operable to maintain a temperature and pressure suitable to facilitate the conversion of the second fraction 117 to a isomerization effluent 132 comprising an increased wt. % of i-C5 and a decreased wt. % of n-C5 relative to the second fraction. In certain embodiments, the second vessel is not required, and a portion of the second fraction is simply diverted via a valve (not depicted) to produce the blending fraction 125. In such embodiments, the quantity of the second fraction that is diverted (if any) is determined by the molecular composition of the second fraction 117 and the quantity of the second fraction that is to be fed to isomerization reactor 127.

Speaking generally, the isomerization reactor contains an isomerization catalyst and is operable to maintain a temperature and a pressure that facilitates the isomerization of at least a portion of the nC5 in the second fraction to iC5 by the isomerization catalyst. The isomerization reaction occurring in the isomerization reactor produces an isomerization effluent that is characterized by an increased ratio of iC5 to nC5 (relative to the corresponding ratio of the hydrocarbon feed stream).

Speaking generally, the isomerization process is designed primarily for continuous catalytic isomerization of the n-C5 present in the second fraction. The process is conducted in an isomerization reactor in the presence of an isomerization catalyst. In certain embodiments, the isomerization catalyst may comprise more than one isomerization catalyst. Optionally, isomerization may be conducted in more than one isomerization reactor arranged in series configuration, with each reactor containing a different isomerization catalyst (or mixture of isomerization catalysts). Each isomerization reactor maintains a partial pressure of hydrogen and operating conditions of temperature and pressure in the isomerization reaction zone that facilitate isomerization by the isomerization catalyst while minimizing hydrocracking.

Ideally, the isomerization catalyst (or catalysts) facilitates the conversion of n-pentane to the higher octane-number isopentane, while any C6 hydrocarbons present may be converted to higher octane 2-3 dimethyl butane (and similar molecules). The isomerization reaction is equilibrium-limited. For this reason, any n-pentane that is not converted on its first pass through the isomerization reactor may optionally be recycled to the isomerization reactor, or converted in multiple isomerization reactors, arranged in series configuration, thereby further increasing the ratio of i-C5 to n-C5 in the product. The relative efficiency of separation of pentane isomers by distillation is poor. Thus, recycling may be more effectively accomplished by a molecular sieve, which selectively adsorbs n-pentane due to its smaller pore diameter relative to isopentane.

In certain embodiments, the activity of the isomerization catalyst may be decreased in the presence of sulfur, thereby decreasing the isomerization rate and, consequently, the octane number of the final product. In such embodiments, the hydrocarbon feed stream is hydrotreated to remove sulfur prior to being conveyed to the isomerization reactor.

Generally speaking, the isomerization catalyst may comprise any known isomerization catalyst. Currently, three basic families of light naphtha isomerization catalysts are known. The first are termed super-acidic catalysts such as, for example, chlorinated alumina catalysts with platinum. Super acidic isomerization catalysts are highly active and have significant activity at temperatures as low as 265° F. (130° C.) using a lower H2/HC ratio (less than 0.1 at the outlet of the reactor). However, maintaining the high acidity of these catalysts requires the addition of a few ppm of chloriding agent to the feedstock. At the inlet of the isomerization reactor, this chloriding agent reacts with hydrogen to form HCl, which inhibits the loss of chloride from the catalyst. Unlike a zeolitic catalyst, the acidic sites on a super-acidic catalyst are irreversibly deactivated by water. These catalysts are also sensitive to sulfur and oxygenate contaminants, so the feed stream is generally hydrotreated and dried to remove residual water contamination. Commercially-available examples of chlorided-alumina catalysts include, but are not limited to, IS614A, AT-2, AT-2G, AT-10 and AT-20 (by Akzo Nobel) and ATIS-2L (by Axens). Due to their chlorinated nature, these are very sensitive to feed impurities, particularly water, elemental oxygen, sulfur, and nitrogen. When using such super-acidic catalysts, the reactor operating temperature generally ranges from 14° C. to 175° C., while the operating pressure is generally in the range from 200 psig to 600 psig, preferably in the range from 425 psig to 475 psig.

Zeolitic isomerization catalysts require a higher operating temperature and are effective at isomerization at temperatures ranging from 220° C. to about 315° C., preferably at a temperature ranging from 230° C. to 275° C. Pressures utilized for isomerization with zeolitic isomerization catalysts typically range from 300 psig to 550 psig with a LHSV from 0.5 to 3.0 hr$^{-1}$. These catalysts react as bifunctional catalysts and require hydrogen at a $H_2$/HC ratio ranging from about 1.5 to about 3. Zeolitic catalysts have advantages over chlorided-alumina catalysts due to zeolitic catalyst tolerance for typical catalyst poisons sulfur, oxygenates and water. Zeolitic catalysts also do not require the injection of a chloriding agent in order to maintain catalyst activity.

A third type of conventional isomerization catalyst that may be useful in certain embodiments comprises sulfated zirconia/metal oxide catalysts. These catalysts are active at relatively low temperatures (e.g., 100° C.) with the advantage of providing enhanced isoparaffin yield. Their biggest drawback is their relative sensitivity to catalyst poisons, especially water. Certainly, other examples of isomerization catalysts that are suitable for use with the present processes and systems described herein are known by those having experience in the field, and thus, require no further disclosure here.

Again, referring to the embodiment disclosed in FIG. 1, the isomerization effluent 132 is conveyed via conduit to be combined with the hydrocarbon feed stream 101 at a location that is upstream of the first separator 110. This allows the additional i-C5 that is produced in the isomerization reactor 127 to be redirected to the activation reactor 133 where it is catalytically activated by the activation catalyst 135.

Generally speaking, in embodiments where the hydrocarbon feed stream includes C6 hydrocarbons, at least a portion of any n-C6 present in the second fraction is isomerized to i-C6 in the isomerization reactor and comprises a portion of the isomerization effluent. This i-C6 forms a component of the second fraction is routed between the first separator and the isomerization reactor until it eventually leaves the system as a component of the blending fraction 125 that is diverted from the second fraction at a point that is located upstream from the isomerization reactor. This serves as an additional advantage of the inventive processes and systems, since i-C6 has a significantly higher octane rating than n-C6 and therefore is a value-added product that can be directly blended into a liquid transportation fuel. A further advantage is that any n-C6 present in the hydrocarbon feed stream is predominantly upgraded by isomerization, which is a more cost-effective method (than catalytic activation) for upgrading n-C6 to higher octane products that are suitable as blend components of a liquid transportation fuel.

Speaking generally, the activation catalyst may comprise a single catalyst, or a mixture of different catalysts that contacts the alkanes present in the isomerization effluent and facilitates at least one of dehydrogenation, cracking, and aromatization of the alkanes, thereby converting at least a portion of hydrocarbons present in the isomerization effluent to produce the activation effluent. Moreover, the activation effluent comprises products that may be utilized as a commodity chemical, an intermediate amenable to further catalytic upgrading, or a transportation fuel (or a component thereof).

Activation catalysts suitable for use with the processes and systems described herein may comprise any catalyst capable of cracking and/or aromatizing hydrocarbons. Favored catalysts include supported or unsupported solid acids, metals, metal chalcogenides, or metal pnictogenides, including (but not limited to) structured and amorphous silica-aluminas, structured and amorphous solid phosphoric acids, clays, other metal oxides, metal sulfates, or metal phosphates, and graphite-supported materials. In certain embodiments, ZSM-5 zeolite catalysts are utilized that are characterized by Si/Al ratios ranging from 12-80, optionally ranging from 35 to 50. Optionally, one or more elements may be impregnated on the zeolite catalyst, including one or more of Ga, Pt, Ni, Mn, Mg, Fe, Cr, P, Cu, La, Sr and F.

Generally speaking, dehydrogenation is not a prerequisite for paraffin activation in the present inventive process. A sufficient concentration of intermediate olefins can be generated through a combination of thermal dehydrogenation and catalytic cracking such that typical dehydrogenation catalyst metals (such as platinum, zinc, molybdenum, or gallium) can be avoided without significantly decreasing product yield. Conventional dehydrogenation catalysts are prone to deactivation by sulfur and nitrogen contaminants that are often present in hydrocarbon feed streams derived from petroleum, so the ability to operate in the absence of these sensitive catalytic materials is highly advantageous to the process.

The present inventive processes and systems take advantage of the differing reactivity of pentane isomers to catalytic activation. Isopentane (i-C5) exhibits catalyst-dependent activation reactivity that is typically greater than that of n-pentane (n-C5), and the optimal activation reactor conditions for the two isomers are therefore distinct. Experimentally, i-C5 can be activated at lower temperatures than n-C5, while maintaining high yields of desired products (such as olefins and aromatics) and decreasing the yield of C1-C4 paraffins (i.e. fuel gas).

For example, utilizing a solid acid activation catalyst at temperature in excess of 550° C., the measured activation rates differ by up to 4 fold in favor of i-C5, when each isomer is contacted with the same catalyst under identical conditions (even in the same reactor simultaneously). Thus, an initial isomerization of the hydrocarbon feed stream to increase i-C5 content, followed by activating the resulting effluent in catalytic activation zone, maximize the yield of value-added, upgraded products (such as olefins and/or aromatics). Increasing conversion of pentane isomers to i-C5 also was found to unexpectedly decrease selectivity of the activation reaction to C1-C4 light gases, which typically have little value other than as fuel gas. This helps maximize the conversion of the feed to upgraded products, which is one of many advantages of the process and systems.

Table 1 (below) illustrates the difference in the activation reactivity of i-C5 versus n-C5 over a microporous silica-alumina activation catalyst. Feed streams comprising either 100 wt. % i-C5 or 100 wt. % n-C5 were each catalytically activated in separate experiments utilizing temperatures of either 600° C. or 550° C. The conversion and product distribution for i-C5 are shown in Table 1, columns 2 and 3, while similar results for the activation of n-C5 are shown in Table 1, columns 4 and 5.

TABLE 1

Product distributions for i-C5 or n-C5 isomer feed streams following conversion by a ⅛" extrudate consisting of 50 wt. % alumina binder and 50 wt. % ZSM-5 zeolite. Activation was performed by contacting the ZSM-5 catalyst with a feed stream comprising either 100 wt. % of i-C5 or 100 wt % of n-C5. Results were time-averaged over 16 hours and all reactions were performed at 1 atm with a WHSV = 4.0 $hr^{-1}$.

| Feed Isomer: | i-C5 | i-C5 | n-C5 | n-C5 |
|---|---|---|---|---|
| Inlet Temperature: | 600° C. | 550° C. | 600° C. | 550° C. |
| Conversion (wt. %): | 94.5 | 82.4 | 78.5 | 48.3 |
| Product Distribution (wt. %) | | | | |
| Hydrogen | 2.4% | 1.6% | 1.1% | 0.4% |
| Methane | 9.8% | 7.8% | 5.3% | 2.3% |
| Ethane | 3.0% | 2.6% | 11.5% | 6.6% |
| Ethylene | 17.4% | 15.6% | 14.3% | 7.7% |
| Propane | 5.3% | 4.8% | 10.6% | 9.9% |
| Propylene | 21.2% | 22.1% | 16.4% | 10.3% |
| Butane | 2.9% | 4.2% | 0.8% | 1.2% |
| Butene | 8.5% | 9.9% | 5.8% | 5.5% |
| Isopentane | 5.5% | 17.6% | 0.1% | 0% |
| n-Pentane | 0% | 0% | 21.5% | 51.7% |
| Pentene | 1.2% | 1.8% | 0.8% | 1.2% |
| C6+ alkanes | 0.0% | 0.3% | 0.0% | 0.0% |
| Benzene | 4.8% | 3.3% | 4.9% | 1.0% |
| Toluene | 11.1% | 6.0% | 5.3% | 1.6% |
| Xylene | 6.4% | 2.2% | 1.3% | 0.6% |
| Ethylbenzene | 0.3% | 0.1% | 0.1% | 0.0% |
| Coke | 0.2% | 0.1% | 0.2% | 0.1% |

The data indicates that when comparing the activation of pentane isomers, conversion of i-C5 to olefins and aromatics is possible at a temperature about 50° C. less than is required for equivalent conversion of n-C5. To be clear, we observed that activation of the i-C5 feed stream at 550° C. converted about the same weight percentage of the feed stream as did activation of n-C5 at 600° C. using the same WHSV. Further, utilizing a decreased temperature of 550° C. for activation of the i-C5 feed stream advantageously decreased the production of C1-C4 light paraffins from 21.0% to 19.4% by increasing the product distribution toward olefins rather than aromatic products. Thus, the ability to separate the i-C5 isomer from n-C5 isomer (and any C6+ hydrocarbons) and activate the i-C5 enriched mixture at relatively reduced temperature, results in approximately equivalent total conversion of the overall feed stream, while decreasing the formation of undesired C1-C4 light paraffins.

The inventive systems and processes take advantage of this reactivity difference between C5 isomers by first isolating, then catalytically-activating predominantly the i-C5 portion of a hydrocarbon feed stream, while simultaneously isomerizing the n-C5/C6+ portion (second fraction) of the feed stream in a first isomerization step. The isomerization effluent (that contains an increased wt. % of i-C5 relative to the second fraction. This maximizes both the conversion yield and selectivity of the activation step to form useful products, including (but not limited to) olefins and aromatics, while minimizing the selectivity of the process to form fuel gas. An additional advantage is that any C6+ hydrocarbons present in the feed stream are predominantly isomerized to produce a value-added liquid transportation fuel blend stock without the need for additional upgrading (e.g., catalytic activation, and optionally, oligomerization or alkylation). Additional advantages will become evident from the detailed disclosure provided below.

Referring again to the embodiment depicted in FIG. 1, the activation effluent 136 is conveyed into a second separator 150 that separates to produce a light hydrocarbons 151 containing four or fewer carbons and hydrogen from a heavy hydrocarbons fraction 152 that predominantly comprises C5 olefins and monocyclic aromatics along with unreacted pentanes and larger C6+ components that were originally present in the hydrocarbon feed stream 101. In certain embodiments, the second separator 150 is a two-phase splitter and separation of the activation effluent 136 is achieved by partial condensation.

Again, referring to the embodiment depicted in FIG. 1, light hydrocarbons 151 predominantly comprises hydrogen as well as C1-C4 hydrocarbons that were not converted in the activation reactor 133. Light hydrocarbons fraction 151 is conveyed to a fourth separator 153 that typically utilizes a conventional separation technology (such as, but not limited to, pressure swing adsorption technology, membrane separation technology, etc.) to separate hydrogen from light hydrocarbons fraction 151 to produce a hydrogen stream 154 and a light paraffins stream 155 that predominantly comprises paraffins containing four or less carbons atoms.

The light paraffins stream 155 is optionally conveyed and mixed with the first fraction to serve as a diluent during catalytic activation of the first fraction 119. In such embodiments, the light paraffins stream 155 is mixed with the first fraction 119 at a point that is upstream from the point where the first fraction 119 contacts the activation catalyst 135 in the activation reactor 133.

In the embodiment depicted in FIG. 1, the heavy hydrocarbons fraction 152 is conveyed to a third separator 160 that is optionally a naphtha stabilizer. The third separator 160 is operable to remove an unreacted C5/C6 fraction 172 comprising predominantly alkanes and olefins containing five to six carbon atoms from the heavy hydrocarbons fraction 152 in order to decrease Reid vapor pressure and increase octane rating of the resulting liquid hydrocarbon product 163, which predominantly comprises hydrocarbon molecules (predominantly monocyclic aromatics) that are characterized by a boiling-point in the range of a liquid transportation fuel, such as, but not limited to, gasoline, diesel and jet fuel. The unreacted C5/C6 fraction 172 may be used directly as a blend component 168 of a liquid transportation fuel, may be mixed with hydrocarbon feed stream 101 at a point that is upstream from first separator 110, or may be mixed with the first fraction 119 (not depicted).

Certain embodiments of the inventive processes and systems convey an activation effluent to an oligomerization reactor containing at least one oligomerization catalyst. The activation effluent contacts the oligomerization catalyst and is converted to larger hydrocarbon products that can be utilized as a component of a liquid transportation fuel, such as, but not limited to: gasoline, diesel and jet fuel. A second embodiment of the inventive processes and systems that includes an oligomerization reactor and additional inventive features is illustrated by the process flow-diagram of FIG. 2. A hydrocarbon feed stream 201 comprising both n-pentane (nC5) and isopentane (iC5) is converted in a system 20. The hydrocarbon feed stream 201 is received by a first separator 210 that operates to separate the feed stream 201 into a first fraction 219 that comprises an increased wt. % of isopentane (i-C5) relative to the hydrocarbon feed stream 201, and a second fraction 217 that comprises an increased wt. % of n-pentane relative to the hydrocarbon feed stream 201. The second fraction 217 further comprises a large majority of any C6 and larger (C6+) hydrocarbons that were originally present in the hydrocarbon feed stream 201. The first separator 210 is operable to separate the i-C5 isomer from the remaining compounds present within the C5-rich hydrocarbon feed stream using conventional separation technology (e.g., distillation). Such methods are conventional, well-understood in the field, and will therefore not be discussed further here. Any separation technology may be used to assist in separating i-C5 from n-C5 to produce the first fraction and the second fraction, and such separation is not considered critical to the inventive process and systems.

Figure 2:
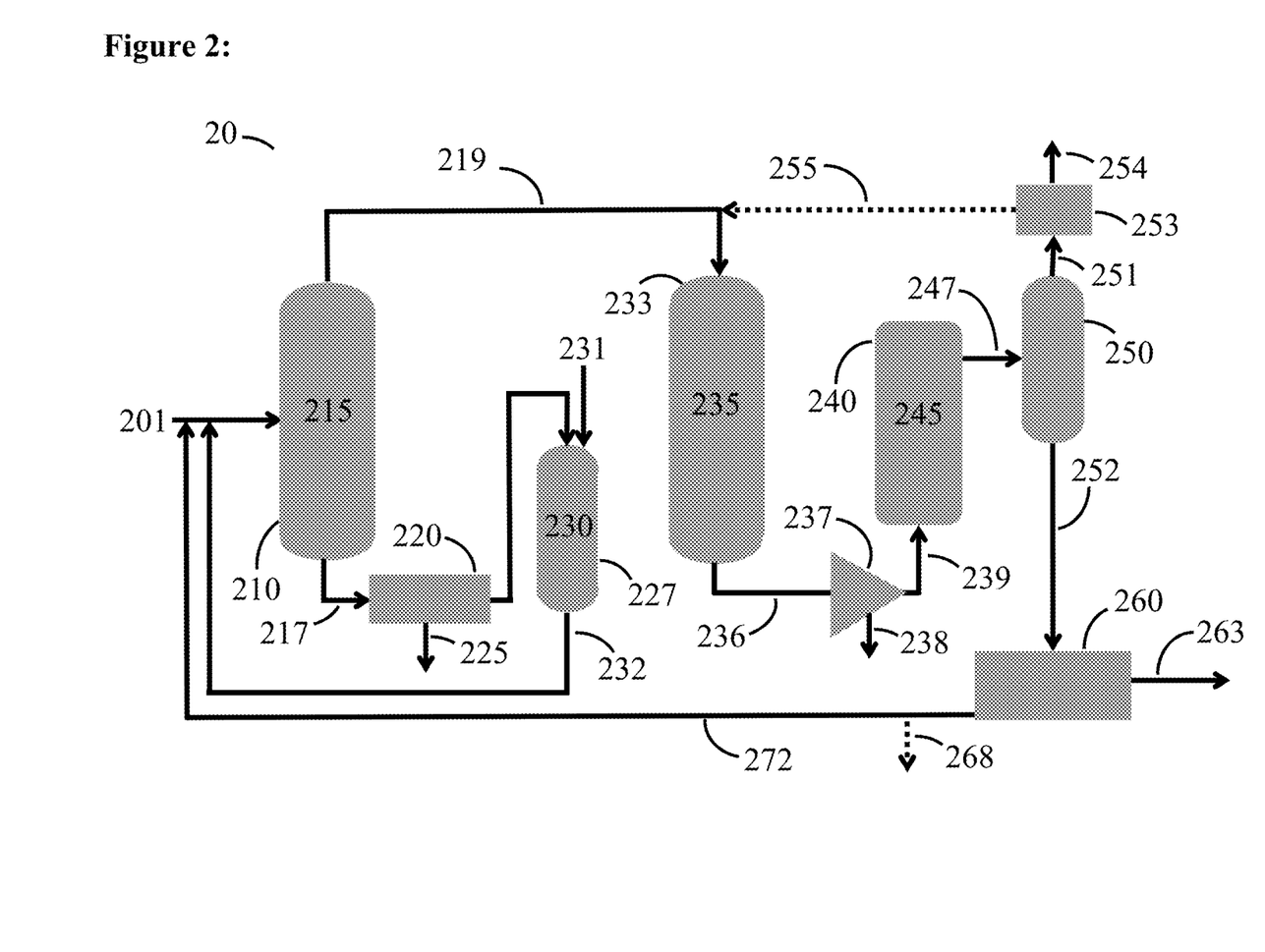
FIG. 2 is a diagram depicting a second embodiment of the inventive processes and systems.

Following separation, the first fraction 219 is conveyed to an activation reactor 233 containing an activation catalyst 235. The activation reactor 233 is operable to maintain a temperature and pressure that is suitable to facilitate conversion of the first fraction 219 to an activation effluent 236.

The activation effluent 236 leaves the activation reactor 233, and is conveyed to compressor/condenser 237, which may comprise one or more functions including a condenser, splitter, compressor and pump. Compressor/condenser 237 is operable to receive and condense at least a portion of the activation effluent 236 to produce a liquid hydrocarbons fraction 238 comprising C6 and larger hydrocarbons including paraffins, olefins and aromatics. The liquid hydrocarbons fraction 238 is removed and may be used as blend stock for a liquid hydrocarbon transportation fuel, while the remaining fraction of the activation effluent 236 is compressed by the compressor/condenser 237 to produce a compressed light hydrocarbons fraction 239 predominantly comprising C1-C5 alkanes and olefins that remains in gaseous phase. In certain embodiments, the compressed light hydrocarbons fraction 239 comprises at least 50 wt. %, at least 60 wt. %, at least 70 wt. %, or at least 80 wt. % of alkanes and olefins containing five or less carbon atoms. The compressed light hydrocarbons fraction 239 is next conveyed to an oligomerization reactor 240 that contains an oligomerization catalyst 245. The compressed light hydrocarbons fraction contacts and is catalytically transformed by the oligomerization catalyst 245 to produce an oligomerization effluent 247 that comprises an increased quantity of hydrocarbon molecules that are characterized by a boiling-point in the range of a liquid transportation fuel (e.g., gasoline and diesel).

Speaking generally, the oligomerization catalyst may comprise any solid catalyst (or mixture of catalysts) characterized as possessing either Brønsted or Lewis acidic properties. In certain embodiments, the oligomerization catalyst is a zeolite or mixture of zeolites, or a reactive transition metal oxide. In certain embodiments, the oligomerization catalyst is ZSM-5, although many zeolites are well-characterized as possessing oligomerization properties and may be suitable for use (either alone or in combination) with the inventive processes and systems described herein. Other well-characterized oligomerization catalysts include, but are not limited to: nickel oxides, aluminum alkyls, aluminum halides, perfluoroaryl boranes, oligomeric methyl aluminoxanes (including supported), perfluoroaryl boranes, fluoroarylanes, trityl borate, ammonium borate (and aluminate salts thereof), supported PhNMe2H+B(C6F5)4- and borate anions and superacidic solid Brønsted acids, among others.

Speaking generally, the oligomerization reactor is maintained at a temperature and pressure suitable to facilitate oligomerization of olefins present in the gaseous activation effluent, thereby producing larger hydrocarbons comprising at least six carbons that are preferably characterized by a boiling point that is in the boiling point range of a liquid transportation fuel (e.g., gasoline or diesel). The oligomerization reactor is generally maintained at a total pressure in a range from 14 psia to 800 psia, optionally in the range from 50 psia to 300 psia. The oligomerization reactor is typically maintained at a temperature (measured within the oligomerization reactor inlet) in the range from 200° C. to 420° C., optionally in the range from 200° C. to 350° C. Typically, flow thorough the oligomerization reactor is maintained at a weight hourly space velocity (WHSV) in the range from 0.5 $hr^{-1}$ to 10 $hr^{-1}$. Optionally, the WHSV is in the range from 0.5 $hr^{-1}$ to 2.0 $hr^{-1}$. While higher overall throughput is desirable, ideally the chosen WHSV allows for conversion of at least 85% of olefins present in the gaseous activation effluent at the selected operating temperature and pressure.

The catalytic conversion occurring in the oligomerization reactor produces an oligomerization effluent that typically comprises an increased quantity of hydrocarbon molecules that are characterized by a boiling-point in the range of a liquid transportation fuel (e.g., gasoline and diesel). Preferably, the combination of isomerization, activation and oligomerization converts at least 30 wt. % of the original hydrocarbon feed stream to hydrocarbon molecules that are characterized by a boiling point that is in the range of gasoline.

Referring again to the embodiment depicted in FIG. 2, the oligomerization effluent 247 produced in the oligomerization reactor 240 is conveyed to a second separator 250 that separates the oligomerization effluent 247 into two fractions: a light hydrocarbons fraction 251 comprising C1-C4 hydrocarbons and hydrogen, and a heavy hydrocarbons fraction 252 comprising hydrocarbons containing at least five carbon atoms (C5+) that may be utilized directly as a blend component of a liquid transportation fuel or an intermediate product that may be additionally processed prior to blending into a liquid transportation fuel.

Again, referring to the embodiment depicted in FIG. 2, light hydrocarbons fraction 251 predominantly comprises hydrogen as well as C1-C4 hydrocarbons that remained unconverted in the oligomerization reactor 240. Light hydrocarbons fraction 251 leaves the second separator 250 and is optionally conveyed to a fourth separator 253 that utilizes a conventional separation technology (such as, but not limited to, pressure swing adsorption technology, membrane separation technology, etc.) to separate hydrogen from the light hydrocarbons to produce a hydrogen stream 254 and a light paraffins stream 255 comprising paraffins containing four or less carbon atoms.

The light paraffins stream 255 is optionally recycled to serve as a diluent during catalytic activation of the first fraction 219. In such embodiments, the light paraffins stream 255 is mixed with the first fraction 219 at a point that is upstream from the point where the first fraction 219 contacts the activation catalyst 235 in the activation reactor 233.

The heavy hydrocarbons fraction 252 is conveyed to a third separator 260 that is optionally a naphtha stabilizer. The third separator 260 is operable to remove an unreacted C5/C6 fraction 272 comprising predominantly alkanes and olefins containing five to six carbon atoms from the heavy hydrocarbons fraction 252 in order to decrease Reid vapor pressure and increase octane rating of the resulting liquid hydrocarbon product 263, which predominantly comprises hydrocarbon molecules (predominantly, monocyclic aromatics) that are characterized by a boiling-point in the range of a liquid transportation fuel, such as, but not limited to, gasoline, diesel and jet fuel. The unreacted C5/C6 fraction 272 may be used directly as a blend component 268 of a liquid transportation fuel, or alternatively, is mixed with hydrocarbon feed stream 201 at a point that is upstream from separator 210. Optionally, at least a portion of the blending fraction 225 as well as the liquid hydrocarbons fraction 238 derived from the condenser/compressor 237 may be combined with the liquid hydrocarbon product 263.

Speaking generally, in certain embodiments, the liquid hydrocarbon product of the process may be hydrotreated in a hydrotreating reactor containing a hydrotreating catalyst in order to reduce olefin and aromatic content in the liquid hydrocarbon product, as well as to remove any nitrogen-containing and sulfur-containing compounds that may be present. The hydrotreating reactor contains at least one hydrotreating catalyst (such as, for example, NiMo, CoMo, etc.) or a precious metal catalyst (such as $Pt/Al_2O_3$, $Pd/Al_2O_3$, or Pd/C, etc) and is maintained at a pressure and temperature suitable for facilitating hydrotreating catalytic reactions. Such processes are conventional in nature, well-understood in the field, and therefore will not be described in greater detail here.

Continuing to refer to the embodiment depicted in FIG. 2, the second fraction 217 is directed to a storage vessel 220 that is operable to both receive the second fraction 217, and to optionally divert at least a portion of the second fraction 217 to produce a blending fraction 225 that may be blended directly into a liquid hydrocarbon transportation fuel (e.g., gasoline). Diverting may be accomplished in a number of conventional ways (e.g., an outlet comprising an adjustable valve) that are well-understood in the art, and thus, will not be discussed further here.

The remainder of the second fraction 217 passes through the storage vessel 220 and is next conveyed to a isomerization reactor 227 that contains an isomerization catalyst 230 and is operable to receive a flow of hydrogen gas 231, and further operable to maintain a temperature and pressure that are suitable to facilitate the conversion of the second fraction 217 by the isomerization catalyst 230 to produce an isomerization effluent 232 that comprises an increased wt. % of i-C5 and a decreased wt. % of n-C5 relative to the second fraction 217.

Speaking generally, certain embodiments of the inventive system and process do not comprise a storage vessel, and a portion of the second fraction is simply diverted via a valve (not depicted) to produce the blending fraction. In such embodiments, the quantity of the second fraction that is diverted (if any) is determined by the molecular composition of the second fraction and the percentage of the second fraction that is to be fed to the isomerization reactor.

Certain embodiments of the inventive processes and systems convey the activation effluent to an aromatic alkylation reactor containing at least one alkylation catalyst. This produces larger hydrocarbon products that can be utilized as either gasoline or diesel transportation fuel, or a component thereof. A third embodiment of the inventive processes and systems that includes an alkylation reactor and additional inventive features is illustrated by the process flow-diagram of FIG. 3. A hydrocarbon feed stream 301 comprising both n-pentane (nC5) and isopentane (iC5) is converted in a system 30. The hydrocarbon feed stream 301 is received by a first separator 310 that operates to separate the feed stream 301 into a first fraction 319 that comprises an increased wt. % of isopentane (i-C5) relative to the hydrocarbon feed stream 301, and a second fraction 317 that comprises an increased wt. % of n-pentane relative to the hydrocarbon feed stream 301. The second fraction 317 further comprises a large majority of any C6 and larger (C6+) hydrocarbons that were originally present in the hydrocarbon feed stream 301. The first separator 310 is operable to separate the i-C5 isomer from the remaining compounds present within the C5-rich hydrocarbon feed stream using conventional separation technology (e.g., distillation). Such methods are conventional, well-understood in the field, and will therefore not be discussed further here. Any separation technology may be used to assist in separating i-C5 from n-C5 to produce the first fraction and the second fraction, and such separation is not considered critical to the inventive process and systems.

Figure 3:
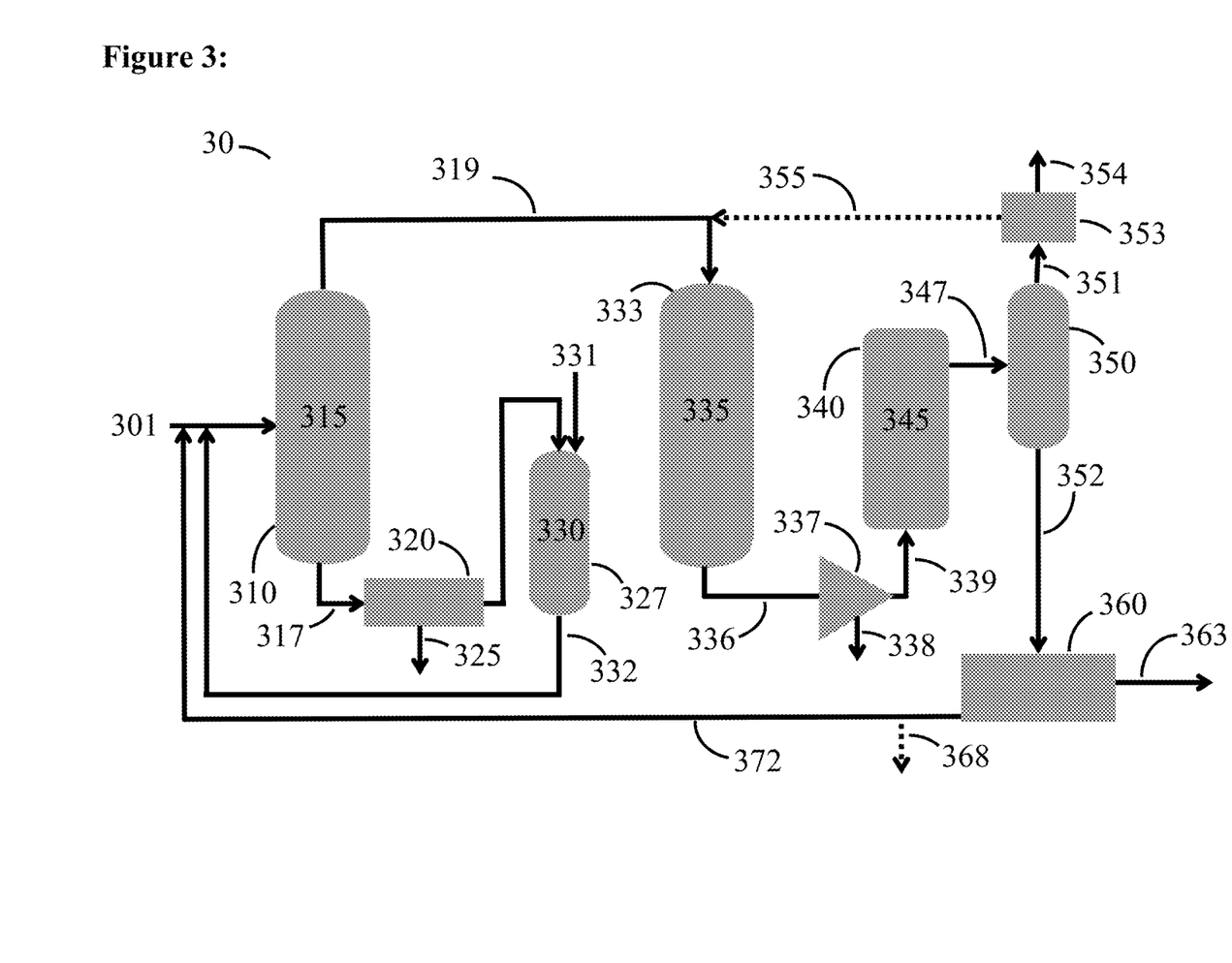
FIG. 3 is a diagram depicting a third embodiment of the inventive processes and systems.

Following separation, the first fraction 319 is conveyed to an activation reactor 333 containing an activation catalyst 335. The activation reactor 333 is operable to maintain a temperature and pressure that is suitable to facilitate conversion of the first fraction 319 to an activation effluent 336. The activation effluent 336 leaves the activation reactor 333, and is conveyed to compressor/condenser 337, which may comprise one or more functions including condensing, splitting, compressing and pumping. Optionally, compressor/condenser 337 is operable to receive and condense a portion of the activation effluent 336 to produce a liquid hydrocarbons fraction 338 comprising C6 and larger hydrocarbons including paraffins, olefins and aromatics. In such embodiments, the liquid hydrocarbons fraction 338 is removed from the system via an outlet in the compressor/condenser 337 and is has the physical and chemical characteristics meeting requirements for a liquid hydrocarbon transportation fuel, or a component thereof. Optionally, the compressor/condenser 337 does not operate to condense the activation effluent. In such embodiments, the entire activation effluent 336 is compressed by compressor/condenser 337.

Following the optional partial condensation of the activation effluent 336, the remaining fraction is compressed by the compressor/condenser 337 to produce a compressed alkylation feed stream 339 comprising gas-phase aromatics (that were not condensed by the compressor/condenser 337) as well as C1-C5 alkanes and olefins. The compressed alkylation feed stream 339 is next conveyed to an alkylation reactor 340 that contains an alkylation catalyst 345. Note that the compressor/condenser 337 does not condense all aromatics present in the activation effluent 336, but instead retains at least a portion of the aromatics to subsequently be alkylated by olefins in the alkylation reactor 340. In alkylation reactor 340 the compressed alkylation feed stream 339 contacts the alkylation catalyst, producing an alkylation effluent that comprises an increased wt. % of alkylated aromatics, especially monocyclic alkylated aromatics.

Speaking generally, the alkylation reactor is maintained at a feed inlet temperature and a pressure that are suitable to facilitate the catalytic alkylation of aromatics that are present in the compressed alkylation feed stream. The aromatics that are alkylated may be produced by aromatization that takes place in the activation reactor or may be a constituent of the hydrocarbon feed stream. Olefins that are used to alkylate the aromatics are mostly produced by the activation of alkanes in the activation reactor. Alkylation of aromatics with light olefins in the alkylation reactor produces an alkylation effluent comprising larger hydrocarbons comprising at least seven carbons that are preferably characterized by a boiling point that is in the boiling point range of a liquid transportation fuel (e.g., gasoline or diesel). Typically, the alkylation effluent comprises an increased percentage of alkylated aromatic compounds comprising from seven to nine carbon atoms. Optionally, the larger hydrocarbons also are characterized by a lower Reid vapor pressure and an increased octane number.

The alkylation reactor is generally maintained at a pressure (measured at the feed inlet) in a range from 14 psia to 800 psia, optionally in the range from 50 psia to 600 psia. The alkylation reactor is typically maintained at a temperature (measured at the alkylation reactor inlet) in a range from 150° C. to 350° C., optionally between 200° C. to 350° C. Typically, flow thorough the alkylation reactor is maintained at a weighted hourly space velocity (WHSV) in the range from 0.5 $hr^{-1}$ to 10 $hr^{-1}$ on a hydrocarbon basis. Optionally, the WHSV is in the range from 0.5 $hr^{-1}$ to 2.0 $hr^{-1}$. While higher overall throughput is desirable, ideally the chosen WHSV allows for conversion of at least 85% olefinic of hydrocarbons present in the mixed effluent at the selected operating temperature and pressure. The catalytic conversion occurring in the alkylation reactor produces an aromatic alkylation reactor effluent that typically comprises at least 30 wt. % (preferably, at least 40 wt %) of hydrocarbon molecules that are characterized by a boiling-point in the range of a liquid transportation fuel.

Speaking generally, the alkylation catalyst may comprise any catalyst characterized as either Brønsted or Lewis acidic. A wide variety of catalysts have been found to promote aromatic alkylation including, but not limited to, aluminum chloride, phosphoric acid, sulfuric acid, hydrofluoric acid, silica, alumina, sulfated zirconia, zeolites (including, for example, ZSM-5, ZSM-3, ZSM-4, ZSM-18, ZSM-20, zeolite-beta, H-Y, MCM-22, MCM-36 and MCM-49). In certain embodiments, the alkylation catalyst simultaneously promotes alkylation of aromatics and oligomerization of olefins present in the mixed effluent.

Referring again to the embodiment depicted in FIG. 3, the alkylation effluent 347 produced in the alkylation reactor 340 is conveyed to a second separator 350 that separates the alkylation effluent 347 into two fractions: a light hydrocarbons fraction 351 comprising C1-C4 hydrocarbons and $H_2$, and a heavy hydrocarbons fraction 352 comprising hydrocarbons containing at least five carbon atoms (C5+) that may be utilized directly as a blend component of a liquid transportation fuel or additionally processed prior to blending into a liquid transportation fuel. Speaking generally, the alkylation effluent preferably comprises an increased quantity (or increased wt %) of alkylated aromatics containing from seven to nine carbon atoms. Preferably, these alkylated aromatics are monocyclic aromatic hydrocarbons.

Again, referring to the embodiment depicted in FIG. 3, light hydrocarbons fraction 351 predominantly comprises hydrogen as well as C1-C4 hydrocarbons that remained unconverted in the alkylation reactor 340. Light hydrocarbons fraction 351 leaves the second separator 350 and is optionally conveyed to a fourth separator 353 that utilizes a conventional separation technology (such as, but not limited to, pressure swing adsorption technology, membrane separation technology, etc.) to separate hydrogen from the light hydrocarbons to produce a hydrogen stream 354 and a light paraffins stream 355 comprising paraffins continuing four or less carbon atoms. The light paraffins stream 355 is optionally recycled to serve as a diluent during catalytic activation of the first fraction 319. In such embodiments, the light paraffins stream 355 is mixed with the first fraction 319 at a point that is upstream from the point where the first fraction 319 contacts the activation catalyst 335 in the activation reactor 333.

The heavy hydrocarbons fraction 352 is conveyed to a third separator 360 that is optionally a naphtha stabilizer. The third separator 360 is operable to remove a unreacted C5/C6 fraction 372 (comprising predominantly alkanes and olefins containing four to six carbon atoms) from the heavy hydrocarbons fraction 352 in order to decrease the Reid vapor pressure and increase the octane rating of the resulting liquid hydrocarbon product 363 that predominantly comprises hydrocarbons (predominantly monocyclic aromatics) that are characterized by a boiling-point in the range of a liquid transportation fuel, such as, but not limited to, gasoline, diesel and jet fuel. The unreacted C5/C6 fraction 372 may optionally be used directly as a blend component 368 of a liquid transportation fuel, or alternatively, is mixed with hydrocarbon feed stream 301 at a point that is upstream from the separator 310. Optionally, at least a portion of the blending fraction 325 and at least a portion of the liquid hydrocarbons fraction 338 derived from the condenser/compressor 337 may be combined with the liquid hydrocarbon product 363.

Speaking more generally, in certain embodiments the liquid hydrocarbon product may be hydrotreated in a hydrotreating reactor containing a hydrotreating catalyst in order to reduce olefin and aromatic content in the liquid hydrocarbon product, as well as to remove nitrogen-containing and sulfur-containing compounds. The hydrotreating reactor contains at least one hydrotreating catalyst (such as, for example, NiMo, CoMo, etc.) or a precious metal catalyst (such as Pt/Al2O3, Pd/Al2O3, or Pd/C, etc) and is maintained at a pressure and temperature suitable for facilitating hydrotreating catalytic reactions. Such processes are conventional in nature and therefore will not be described in greater detail here.

Certain embodiments comprise mixing a diluent with the first fraction prior to contacting the resulting mixture with an activation catalyst in the activation reactor. The diluent may be added in a ratio ranging from 10:1 to 1:10 molar ratio relative to the quantity of isomerization effluent fed to the activation reactor. The diluent may be added at any point that is upstream from, or within, the activation reactor, but prior to contacting the activation catalyst.

The diluent may comprise any substance that is less chemically-reactive with the activation catalyst than the constituents that are present in the first fraction at the conditions of temperature and pressure that are maintained within the activation reactor. This prevents the diluent from reacting with the activation catalyst. Such properties are found in a large number of substances that are fully within the grasp of a person who is knowledgeable in the field. In certain embodiments, the diluent may comprise C1-C4 light paraffins, including recycling C1-C4 light paraffins produced by the inventive processes and systems described herein. In certain embodiments, the diluent may comprise any of methane, ethane, propane, butanes, benzene, toluene, xylenes, alkyl- or dialkyl-benzenes, naphthenes, C2-C5 olefins, and combinations thereof.

The presence of diluent during catalytic activation (i.e., activation) provides numerous advantages. First, it effectively decreases the concentration of the isomerization effluent within the activation reactor. This results in a small increase in the total conversion of alkanes to olefins or aromatics within the activation reactor. However, it also increases the selectivity toward the production of olefins, while slightly decreasing the selectivity toward the production of aromatics. Adjusting the ratio of diluent to isomerization effluent changes the ratio of olefins to aromatics in the resulting activation effluent, thereby providing a valuable point of operational control for downstream processes. Typically, the optimal molar production ratio of olefins to aromatics ranges from about 0.5:1 to about 1.5:1, in order to maximize the value captured in the olefin intermediates during the alkylation in the alkylation reactor. Mono-alkylated aromatics exhibit beneficial (increased) octane rating and vapor pressure for application as blending components in certain transportation fuels such as gasoline. In contrast, di-alkyl and tri-alkyl aromatics comprising more than nine carbon atoms are not well-suited for blending into gasoline, and exhibit nonoptimal cetane number for blending into diesel.

Addition of a diluent also advantageously favors the production of value-added olefins relative to C1-C4 light paraffins and also mitigates dimerization of C5 hydrocarbons to form durene (1,2,4,5-tetramethylbenzene), a problematic byproduct that often precipitates from gasoline blends.

EXAMPLES

The following examples are representative of certain embodiments of the inventive processes and systems disclosed herein. However, the scope of the invention is not intended to be limited to the embodiment specifically disclosed. Rather, the scope is intended to be as broad as is supported by the complete disclosure and the appending claims.

Example 1

This example demonstrates the preliminary rationale for isomerizing at least a portion of the n-C5 found in a given hydrocarbon feed stream to i-C5 prior to contacting the pentane with an activation catalyst. The graphs below illustrate differences in activation reactivity for n-C5 and i-C5. Feed streams were utilized that comprised either 100 wt. % i-C5 (i-C5), 100 wt. % n-C5 (n-C5), or a 70 wt. % iC5/30 wt. % n-C5 mixture (i/n [7:3]) that represents an isomerized pentanes stream that has been contacted with an isomerization catalyst to increase the ratio of i-C5 to n-C5. The catalyst utilized was ⅛" extrudate consisting of 50 wt. % alumina binder and 50 wt. % ZSM-5 zeolite, and experiments were conducted at a WHSV of 1.3 $hr^{-1}$ at 1 atm. Results were averaged over the total time on stream of 16 hr.

Figure 4:
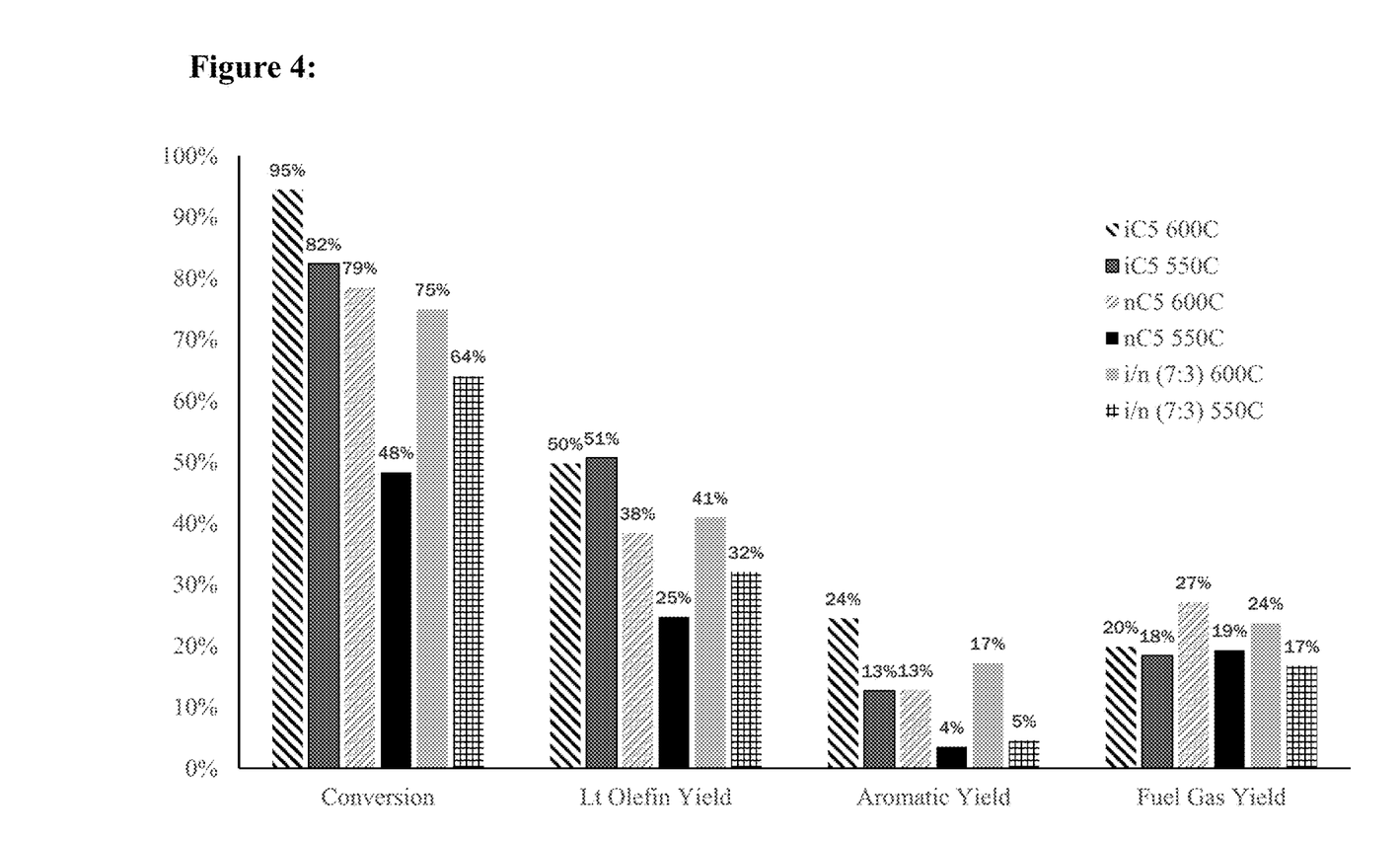
FIG. 4 is a bar graph depicting product selectivity resulting from catalytic activation of either n-pentane or iso-pentane at two different temperatures.
Figure 5:
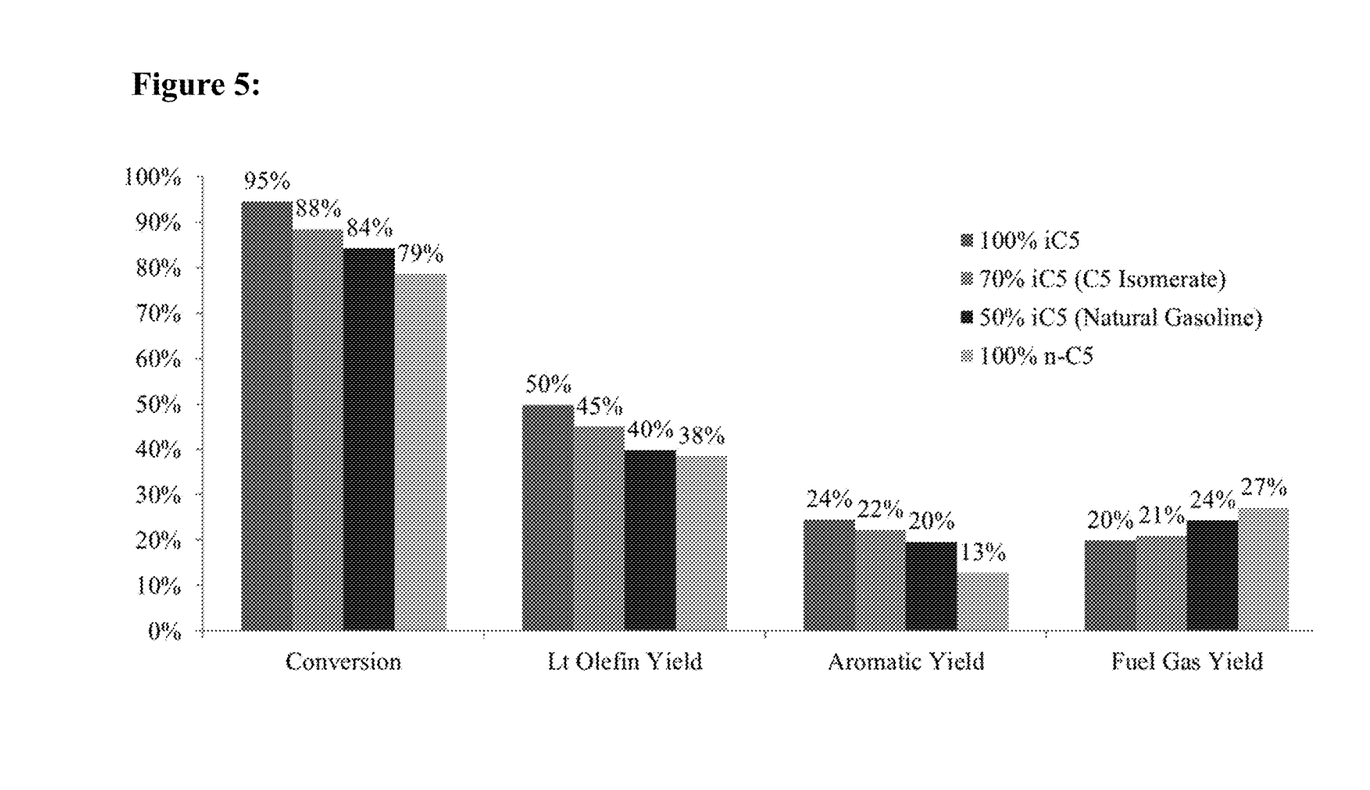
FIG. 5 is a bar graph showing the effect of isomerization of the feed stream on the total conversion and product yield for a first feed stream comprising a 1:1 ratio of n-C5 to i-C5, and a second feed stream comprising a 7:3 ratio of n-C5 to i-C5.
Figure 6:
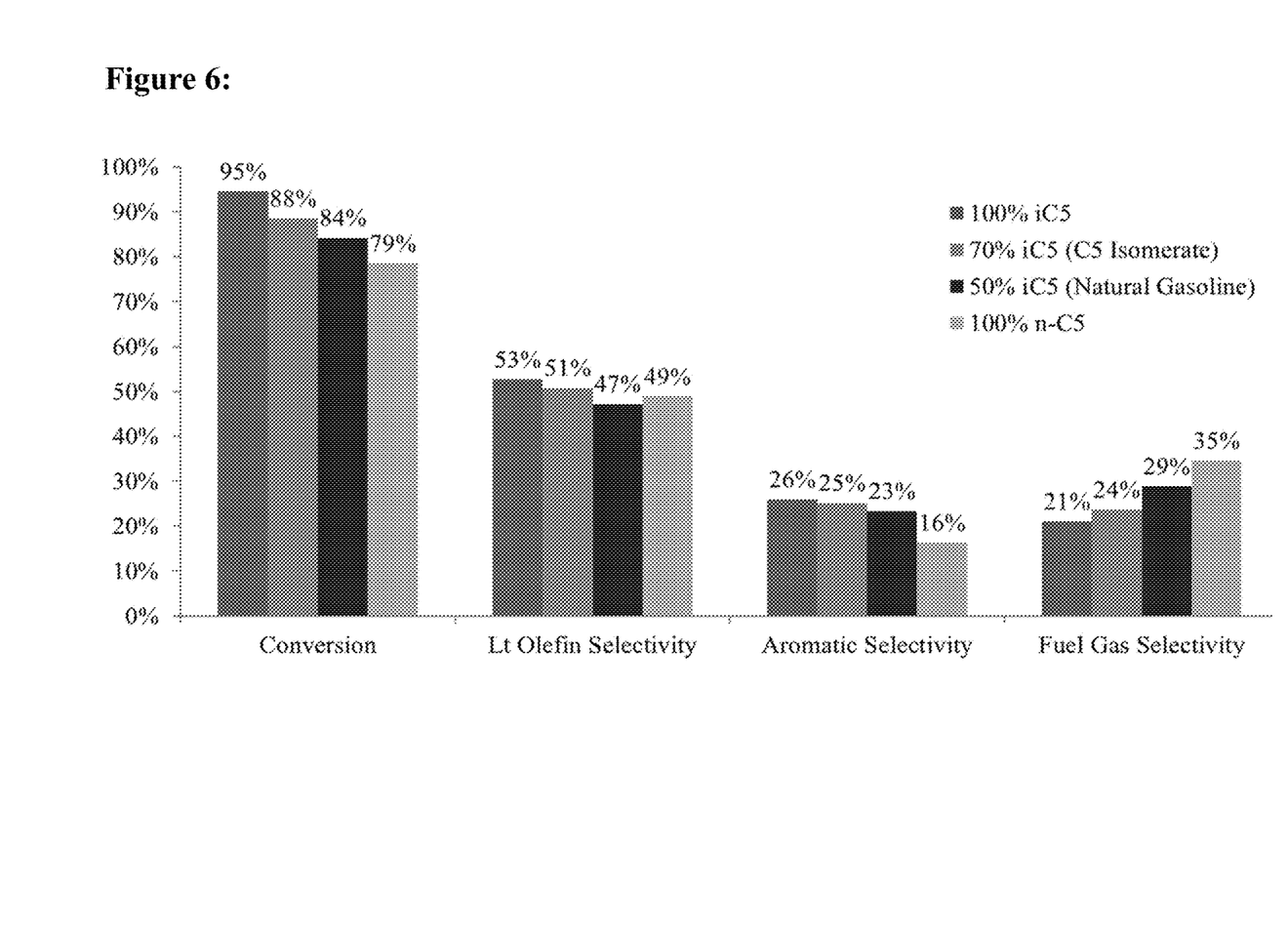
FIG. 6 is a bar graph showing the effect of isomerization of the feed stream on the total conversion and product selectivity for a first feed stream comprising a 1:1 ratio of n-C5 to i-C5, and a second feed stream comprising a 7:3 ratio of n-C5 to i-C5.

FIG. 4 is a bar graph depicting the results of catalytically activating each feed stream at either 550° C. or 600° C. The graph depicts, as percentages, the total catalytic conversion of each feed stream (first column) the yield to light olefins as product (second column), the yield to aromatics as product (third column) and the yield to C1-C4 light paraffins (defined as non-olefin hydrocarbons containing from one to four carbon atoms), fourth column. Yield was calculated on a wt. % basis, relative to the weight of the feed stream.

The results demonstrate that an effective conversion (82%) of a the i-C5 fraction was achieved at 550° C., while a similar level of n-C5 conversion (79%) required a temperature of 600° C. Activating the i-C5 fraction at 550° C. (instead of 600° C.) also increased the yield towards the production of olefins while decreasing the aromatics yield. Lastly, these changes in yield caused no significant increase in the production of byproduct C1-C4 light paraffins. Meanwhile, the activation/conversion of n-C5 at 550° C. only converted 48% of the feed, while the undesirable production of fuel gas (C1-C4 light paraffins) was higher compared to the same activation/conversion performed on a 100% i-C5 feed stream. The results for the 7:3 ratio feed of i-C5 to n-C5 demonstrates the advantages of increasing the amount of i-C5 in the feed that is fed to the activation reactor, as it shows many of the same benefits demonstrated for the 100% i-C5 feed.

Example 2

This experiment demonstrates that isopentane (i-C5) is advantageously converted by both an activation catalyst and a subsequent oligomerization catalyst to produce a high percentage of product that is suitable for use as a liquid transportation fuel. A 100 wt. % i-C5 feed stream was upgraded by first contacting it with a zeolite activation catalyst, followed by contacting a zeolite oligomerization catalyst. Activation was conducted by contacting the feed stream with ⅛ in. diameter catalyst extrudate consisting of 50 wt. % alumina binder and 50 wt. % ZSM-5 zeolite catalyst at a temperature of 579° C., and a WHSV of 2.6 hr$^{-1}$ at 1 atm.

Oligomerization was conducted by contacting the activation effluent with a ZSM-5 zeolite catalyst in a reactor where the inlet temperature for the activation effluent was maintained at 250° C., the pressure was 1 atm, and the WHSV for the feed stream was 1.3 hr$^{-1}$. Results were time-averaged over 16 hours. The table shows the product distribution following conversion along with the selectivity to olefins and liquid product. The term "selectivity" indicates the percentage of the catalytically converted feed stream that was converted to a particular product.

TABLE 2

Upgrading pentanes by activation alone or activation plus oligomerization.

|  | Activation | Activation + Oligomerization |
|---|---|---|
| Total Conversion (wt. %) | 88 | 87 |
| C1-C4 Light paraffins Yield | 32 | 32 |
| Upgraded Product Yield (wt. %) | 55 | 54 |
| Total Coke Yield (wt. %) | 0.1 | 0.1 |
| Light Olefin Yield (wt. %) | 42 | 16 |
| Light Olefin Selectivity (wt. %) | 48 | 19 |
| Liq. Yield (wt. %) | 13 | 38 |
| Liq. Product Selectivity (wt. %) | 15 | 44 |

The data in Table 2 show that the subjecting the effluent from the first activation reactor to a subsequent oligomerization step in a second reactor increased the liquid product yield from 13 wt. % to 38 wt. %. This liquid product yield represents a liquid product suitable for blending into a liquid transportation fuel such as gasoline (up from 13 wt. % prior to oligomerization), and that selectivity to liquid product for the portion of the feed stream that was converted was 44 wt. %. Undesirable C1-C4 light paraffins production was limited to 32 wt. % of the original feed stream, which optionally may be recycled to be either activated or to serve as a diluent in at least one of the activation reactors. Further, the final product only comprised 16 wt. % of light olefins, (primarily ethylene), which may be recycled to the process, or diverted to be utilized in any of a variety of conventional processes.

Example 3

This experiment demonstrates that isopentane (i-C5) is advantageously converted by both an activation catalyst and a subsequent alkylation catalyst to produce a high percentage of product that is suitable for use as a liquid transportation fuel. A 100 wt. % i-C5 feed stream was upgraded by first contacting it with a zeolite activation catalyst, followed by contacting the activation effluent with a zeolite alkylation catalyst. Activation was conducted by contacting the feed stream with a ⅛ in. diameter catalyst extrudate consisting of 50 wt. % alumina binder and 50 wt. % ZSM-5 zeolite catalyst in an activation reactor. The temperature of the activation reactor at the inlet for the feed stream was 579° C., the pressure was 1 atm, and the WHSV for the feed stream was 2.6 hr$^{-1}$. Alkylation was then conducted by contacting the effluent with a ZSM-5 catalyst in a reactor where the temperature at the inlet for the feed stream was 230° C., the pressure was maintained at 15 psig and the WHSV of the feed stream was 1.3 hr$^{-1}$ at 1 atm. Results were time-averaged over 16 hours. The table shows the product distribution following conversion along with the selectivity to olefins and liquid product. The term "selectivity" indicates the percentage of the catalytically converted feed stream that was converted to a particular product.

TABLE 3

Upgrading isopentane by activation only or activation followed by alkylation.

|  | Activation | Activation + Alkylation |
|---|---|---|
| Total Conversion (wt. %) | 87 | 88.3 |
| Light paraffins Yield (wt. %) | 32.0 | 23.9 |
| Light Paraffins Selectivity | 35.5 | 27.0 |
| Upgraded Product Yield (wt. %) | 55.0 | 64.4 |
| Total Coke Yield (wt. %) | 0.1 | 0.2 |
| Light Olefin Yield (wt. %) | 42.0 | 14.4 |
| Light Olefin Selectivity (wt. %) | 48.0 | 16.3 |
| Liquid Yield (wt. %) | 13.0 | 50.0 |
| Liquid Product Selectivity | 15.0 | 56.7 |

The data in Table 3 show that subjecting the activation effluent to a subsequent alkylation step increased the liquid product yield from 13.0 wt. % to 50 wt. %. This liquid product is suitable for blending into a liquid transportation fuel such as gasoline, and possesses an increased research octane number, a suitable distillation T50 and endpoint, and low vapor pressure. Selectivity to liquid product for the portion of the feed stream that was converted increased from 15.0 wt. % to 56.7 wt. %. Undesirable C1-C4 light paraffins production was limited to 23.9 wt. % of the feed stream, a portion of which could be used as diluent for the inventive processes and systems. Further, the final product only comprised 16.3 wt. % of light olefins. These olefins may be recycled to the activation reactor, used as a diluent in the alkylation reactor, or diverted to be utilized in any of a variety of conventional processes.

Note that the results shown in the above table may underestimate the total percentage of a mixed pentanes feed stream that would be available for blending into a liquid transportation fuel, as a typical hydrocarbon feed stream (such as, but not limited to, natural gasoline) may also include an excess quantity of C5/C6+ that would not be either catalytically-cracked or introduced into the alkylation reactor, but would partition into the second fraction and leave the system via an outlet located upstream from the isomerization reactor. This excess quantity of C5/C6+ is suitable for direct blending into the liquid hydrocarbon product. In certain embodiments, a portion of the nC5/C6+ fraction is diverted when necessary to achieve the desired 0.5:1 to 1.5:1 olefin to aromatic ratio that maximizes production of mono-alkylated aromatics in the alkylation reactor.

Example 4

Analysis of the product created in Example 3 by first activating, then alkylating a 100 wt. % i-C5 feed stream revealed the composition shown in Table 4:

TABLE 4

Product composition and fuel characteristics for a 100 wt. % i-C5 feed stream that was activated at a temperature of 600° C. (WHSV = 2.6 hr$^{-1}$) followed by alkylation at a temperature of 230° C. (WHSV 1.3 hr$^{-1}$)

| Component | Quantity (wt. %) |
|---|---|
| Paraffin | 3.0% |
| iso-Paraffin | 9.7% |
| Aromatics | 67.0% |
| Mono-cyclic Aromatics | 63.9% |
| n-Olefins | 1.1% |
| iso-Olefins | 4.4% |
| Research Octane Number (calculated) | 98.0 |
| Motor Octane Number (calculated) | 89.6 |

It is clear that the final product comprises a high wt. percentage of monocyclic aromatics that are an exceptional blend stock for a gasoline (see calculated Research Octane and Motor Octane Numbers, above). Only a small quantity of paraffins remain, which can be recycled to process, used as diluent for the activation step, or combusted to produce at least a portion of the heat required for the process.

Example 5

This example demonstrates the effect that a methane diluent has on catalytic activation and conversion of two different hydrocarbon feed streams: 1) a simulated "natural gasoline" comprising 50 wt. % i-C5 and 50 wt. % n-C5 isomers, and 2) a simulated "first fraction" comprising 70 wt. % i-C5 and 30 wt. % n-C5. Each of the two feed streams were fed at a WHSV of 1.3 hr$^{-1}$ to a reactor containing an activation catalyst comprising a ⅛" extrudate consisting of 50 wt. % alumina binder and 50 wt. % ZSM-5 zeolite. The temperature of the reactor (at the inlet for the feed stream) was maintained at 600° C. and 20 psig (2.4 Bar) and results were time-averaged for 16.5 hr. For certain reactions, methane diluent was co-fed along with each feed stream at a methane:feed stream molar ratio of 2:1.

The reaction produced an effluent comprising light olefins, aromatics and light paraffins. Table 5 (below) shows the effect of the methane diluent on the total conversion of the 1:1 and 7:3 feed streams, respectively, as well as the selectivity of each conversion toward light olefins, aromatics, and byproduct C1-C4 fuel gas.

TABLE 5

Catalytic activation of a 1:1 i-C5:n-C5 feed stream and a 7:3 1 i-C5:n-C5 feed stream in both the absence and presence of methane diluent.

| Feed Stream | 1:1 i-C5:n-C5 | 1:1 i-C5:n-C5 | 7:3 1 i-C5:n-C5 | 7:3 1 i-C5:n-C5 |
|---|---|---|---|---|
| +/−Diluent | No Diluent | CH$_4$ Diluent | No Diluent | CH$_4$ Diluent |
| Material Balance | 101% | 103% | 102% | 101% |
| Conversion | 92% | 80% | 93% | 81% |
| Fuel gas yield | 37% | 22% | 34% | 21% |
| Product Yield | 54% | 58% | 58% | 60% |
| Coke Yield | 0% | 0% | 0% | 0% |
| Lt. Olefin Yield | 34% | 44% | 35% | 43% |
| Lt. Olefin Selectivity | 37% | 55% | 38% | 53% |
| Aromatic Yield | 20% | 14% | 22% | 17% |
| Aromatic Selectivity | 21% | 17% | 24% | 21% |
| Fuel Gas Yield | 37% | 22% | 34% | 21% |
| Fuel Gas Selectivity | 41% | 27% | 37% | 26% |

The data in Table 5 indicate that adding inert diluent caused slight loss of overall conversion, but significantly increased the yield and selectivity to light olefin production for both the 1:1 and 7:3 feed streams. Adding inert diluent also greatly diminished selectivity to production of C1-C4 fuel gas. Meanwhile, only a small drop in selectivity to aromatics production was observed for the 1:1 ratio feed stream in the presence of diluent, which was offset by an equivalent increase in aromatics production in the 7:3 ratio feed stream (in the presence of diluent). All of these results are advantageous to the process, particularly in certain embodiments where the mixed effluent is immediately utilized as feed stream for either an oligomerization or alkylation process. In certain embodiments that comprise an oligomerization process, diluent is added to the activation feed stream at a ratio that maximizes light olefin production, providing an advantageous feed stream for the oligomerization catalyst. In certain embodiments that comprise an aromatic alkylation process, diluent can be added to the activation feed stream at a ratio that produces a first effluent comprising olefins and aromatics at a ratio (typically between 0.5:1 and 1.5:1 by mole) that provides an advantageous feed stream for an aromatic alkylation process.

In closing, it should be noted that the discussion of any reference is not an admission that it is prior art to the present disclosure, in particular, any reference that may have a publication date after the priority date of this application. Although the systems and processes described herein have been described in detail, it is understood that various changes, substitutions, and alterations can be made without departing from the spirit and scope of the invention as defined by the following claims.

Definitions:

In the present disclosure, the term "conversion" is defined as any of the chemical reactions that occur during upgrading of hydrocarbons to liquid transportation fuels. Examples of such reactions include, but are not limited to: oligomerization, aromatization, dehydrogenation, alkylation, hydrogenation and cracking.

We claim:

1. A method for converting a feed stream comprising pentanes to produce a blend component of liquid transportation fuel, the method comprising:
   a) providing a hydrocarbon feed stream comprising at least 50 wt. % pentanes, including both n-pentane and isopentane;
   b) at least partially separating the hydrocarbon feed stream in a separator to produce:
      a first fraction that comprises at least 80% of the isopentane present in the hydrocarbon feed stream (on a molar basis), and that further comprises at least 90% of hydrocarbons present in the hydrocarbon feed stream (on a molar basis) that are characterized by a vapor pressure equal to or greater than the vapor pressure of isopentane, and
      a second fraction that comprises at least 80% of the n-pentane content of the hydrocarbon feed stream (on a molar basis) and at least 90% of hydrocarbons from the hydrocarbon feed stream that contain six or more carbons (on a molar basis);
   Step c): contacting the first fraction with an activation catalyst at a temperature and a pressure that facilitates catalytic activation of at least a portion of the first fraction by the activation catalyst to produce an activation effluent comprising olefins containing from two to five carbon atoms, monocyclic aromatics and unconverted hydrocarbons containing from two to five carbon atoms;

Step d): removing a first portion of the second fraction as the blend component of liquid transportation fuel;

e) contacting a second portion the second fraction with at least one isomerization catalyst in an isomerization reactor that is maintained at a temperature and a pressure that facilitates the isomerization of at least a portion of n-pentane in the second fraction to produce isopentane, thereby producing an isomerization effluent characterized by an increased ratio of isopentane to n-pentane (on a wt. % basis) relative to the isopentane to n-pentane ratio of the hydrocarbon feed stream;

f) combining the isomerization effluent with the hydrocarbon feed stream of a).

2. The method of claim 1, additionally comprising compressing and at least partially condensing the activation effluent to produce a liquid hydrocarbons fraction that comprises monocyclic aromatics and unreacted hydrocarbons containing at least five carbon atoms, and a compressed light hydrocarbons fraction that comprises hydrogen and at least 80 wt. % hydrocarbons containing four or less carbon atoms.

3. The method of claim 2, further comprising separating the liquid hydrocarbons fraction into an liquid hydrocarbon product and an unreacted C5/C6 hydrocarbons fraction, wherein the liquid hydrocarbon product comprises monocyclic aromatics the unreacted C5/C6 hydrocarbons fraction comprises alkanes and olefins containing from five to six carbons.

4. The method of claim 3, wherein the unreacted C5/C6 hydrocarbons fraction is mixed with the hydrocarbon feed stream of a).

5. The method of claim 2, wherein the compressed light hydrocarbons fraction is separated to produce a hydrogen stream and a light paraffins stream comprising paraffins containing four or less carbon atoms.

6. The method of claim 5, further comprising adding a diluent to the first fraction prior to the contacting of c), wherein the diluent is characterized as less chemically reactive with the activation catalyst than the first fraction at the conditions of temperature and pressure that are maintained in the activation reactor and wherein at least a portion of the light paraffins stream is mixed with the first fraction and serves as the diluent.

7. The method of claim 1, wherein the hydrocarbon feed stream comprises at least 70 wt. % pentanes.

8. The method of claim 1, wherein the activation catalyst comprises one or more zeolites characterized by a Si/Al ratio ranging from 12 to 80.

9. The method of claim 1, wherein the activation catalyst comprises ZSM-5 zeolite.

10. The method of claim 1, wherein the activation catalyst facilitates carbon-hydrogen bond activation that leads to at least one of olefination, dimerization, oligomerization and aromatization of the first fraction.

11. The method of claim 1, wherein the temperature in the activation reactor is maintained at a temperature in the range from 500° C. to 625° C. and a pressure in the range from 15 psig to 100 psig.

12. The method of claim 1, wherein the temperature in the activation reactor is maintained at a temperature in the range from 550° C. to 600° C. and a pressure in the range from 20 psig to 60 psig.

13. The method of claim 1, wherein the temperature in the activation reactor is maintained at a temperature in the range from 550° C. to 575° C. and a pressure in the range from 20 psig to 50 psig.

14. The method of claim 1, further comprising adding a diluent to the first fraction prior to the contacting of c), wherein the diluent is characterized as less chemically reactive with the activation catalyst than the first fraction at the conditions of temperature and pressure that are maintained in the activation reactor.

15. The method of claim 14, wherein the diluent is added in an amount that alters the specificity of the activation catalyst to increase the production of olefins, decrease the production of aromatics, or combinations thereof, thereby increasing the ratio of olefins to aromatics in the activation effluent.

16. The method of claim 14, wherein the diluent is added in an amount that is effective to produce an activation effluent that is characterized by an olefins to aromatics ratio in the range of 0.5 to 2.0.

17. The method of claim 14, wherein the diluent is added in an amount that is effective to produce an activation effluent that is characterized by an olefins to aromatics ratio in the range of 0.5 to 1.0.

18. The method of claim 14, wherein the diluent is selected from at least one of methane, ethane, propane and butane isomers.

19. The method of claim 1, further comprising adding a diluent to the first fraction prior to the contacting of c), wherein the diluent is characterized as chemically non-reactive with the activation catalyst at the conditions of temperature and pressure that are maintained in the activation reactor.

20. The method of claim 1, wherein wherein step e) comprises multiple isomerization reactors that are arranged in series configuration, wherein each of the multiple reactors contains at least one isomerization catalyst and is maintained at a temperature and a pressure that facilitates the isomerization of n-pentane to isopentane by the at least one isomerization catalyst.

* * * * *